United States Patent [19]

Sulzbach

[11] 4,358,348
[45] Nov. 9, 1982

[54] PROCESS FOR THE PREPARATION OF PURE HEXAFLUOROPROPYLENE OXIDE

[75] Inventor: Reinhard A. Sulzbach, Burghausen, Fed. Rep. of Germany

[73] Assignee: Hoechst Aktiengesellschaft, Fed. Rep. of Germany

[21] Appl. No.: 352,347

[22] Filed: Feb. 25, 1982

[30] Foreign Application Priority Data

Mar. 3, 1981 [DE] Fed. Rep. of Germany ....... 3107967

[51] Int. Cl.$^3$ ..................... B01D 3/40; C07D 301/32
[52] U.S. Cl. ...................................... 203/67; 549/541
[58] Field of Search .......................... 203/67; 549/541

[56] References Cited

U.S. PATENT DOCUMENTS

| 3,101,304 | 8/1963 | Wiist | 203/67 |
| 3,326,780 | 6/1967 | Wiist | 203/67 |
| 4,134,796 | 1/1979 | Oda et al. | 549/541 |

*Primary Examiner*—Wilbur L. Bascomb, Jr.
*Attorney, Agent, or Firm*—Connolly and Hutz

[57] ABSTRACT

The separation of mixtures of hexafluoropropylene oxide and hexafluoropropylene is effected by extractive distillation in the presence of methylene chloride, whereby an excellent separating effect is achieved at a low energy consumption.

1 Claim, No Drawings

PROCESS FOR THE PREPARATION OF PURE HEXAFLUOROPROPYLENE OXIDE

The invention relates to a process for the purification of hexafluoropropylene oxide (HFPO) from mixtures composed of HFPO and hexafluoropropylene (HFP), by extractive distillation in the presence of an extractive medium.

HFPO is prepared by oxidizing HFP, for which a number of processes, using a variety of oxidizing agents, are known. It is common to all these processes that they only result in a partial conversion of HFP, ie. mixtures of the HFPO which has been formed and of unreacted HFP are produced. The unreacted HFP has to be separated off as quantitatively as possible from these mixtures and recycled to the oxidation process, before the HFPO is processed further. However, this separation is difficult.

Attempts have already been made to separate off the HFP present in such mixtures by conversion into its dibromide followed by distillation (German Pat. No. 1,240,516). However, this involves either the loss of an expensive substance or recovering it expensively from the dibromide.

The preparation of HFPO in a pure state by distillation from mixtures with HFP is not easy to carry out technically, since the physical of the two components determining the separation are very similar. Separation by distillation alone would require a distillation column over 80 m in length because the boiling points are close to one another (HFP $-29.4°$ C., HFPO $-27.4°$ C.).

There has, therefore, been no lack of endeavours to reduce the volatility of HFP, and thus to increase the relative volatility of the HFPO, by adding a solvent. U.S. Pat. No. 3,326,780 describes a process for purifying HFPO by removing HFP by means of extractive distillation; in this purpose the distillation is carried out in the presence of alkyl-substituted or alkoxy-substituted benzenes which are mono-, di- or tri-substituted by alkyl or alkoxy groups having 1 to 4 carbon atoms, in the presence of dialkyl ethers of ethylene glycol or diethylene glycol wherein the alkyl groups of the ethers have 1 to 2 carbon atoms, or in the presence of carbon tetrachloride or chloroform. Furthermore, British Pat. No. 1,543,174 describes a process for purifying HFPO by separating the HFPO from HFP by extractive distillation in the presence of a compound normally liquid in order to increase the relative volatility; in this process the normally liquid compound which is employed is a chlorinated hydrocarbon having at least 2 carbon atoms or a dialkyl ether having at least one alkyl group which is branched and contains at least 3 carbon atoms.

By using a solvent which affects the relative volatility (an extractive medium) it is possible to reduce considerably the size of the equipment required for the separation of HFPO and HFP, which results in a considerable reduction in cost. Whereas separation by distillation alone would require a column over 80 m in length, a column having an absorption section only 5 to 12 m in length is adequate if the process of extractive distillation is used. This corresponds to about 20 to 50 theoretical plates.

However, the saving in capital costs which results if the process of extractive distillation is used instead of the process of straight distillation, is frustrated by an increased consumption of energy which is required for heating and cooling the recycled extractive medium, particularly if the extractive medium is not cooled with cooling water, but is cooled with cooling brine to temperature below 15° C., in order to increase the solubility of the gas.

The present invention is based on the object of reducing consumption of energy required for separating HFPO and HFP by the process of extractive distillation, by employing an extractive medium which is superior in its separating effect to the compounds hitherto described.

This object is achieved by means of a process for the removal of HFPO from gas mixtures composed of HFPO and HFP by extractive distillation in the presence of an extractive medium, which comprises bringing the gas mixture into contact with methylene chloride as the extractive medium, whereupon HFPO is evolved in the form of gas, and HFP is absorbed and is then liberated by heating the methylene chloride to its boiling point.

It has been found, surprisingly, that methylene chloride possesses a better separation efficiency and is more suitable for the separation of HFPO and HFP than the chlorinated hydrocarbons already described for this purpose, which have 1 or 2 carbon atoms, such as, for example, chloroform, carbon tetrachloride, 1,2-dichloroethane or trichloroethylene.

The relative volatility of HFP/HFPO, defined as the solubility of HFP gas, divided by the solubility of HFPO gas (measured in $cm^3$ per g of solvent and per bar at 20° C.) is 20 to 30% higher if methylene chloride is employed than if other homologous chlorinated hydrocarbons are used. The relationships can be seen in the following table:

| Extractive medium | Relative volatility (HFP/HFPO) |
| --- | --- |
| Methylene chloride | 2.14 |
| Chloroform | 1.77 |
| 1,2-Dichloroethane | 1.72 |
| Carbon tetrachloride | 1.67 |
| Trichloroethylene | 1.49 |

Since the energy consumption needed to separate HFP and HFPO decreases in strict proportion as the relative volatility increases, an energy saving of 20 to 30% is achieved if methylene chloride is employed instead of the chlorinated hydrocarbons hitherto employed for the separation.

In addition, as an extractive medium for this separation, methylene chloride also has a number of advantages which, in general, are not applicable, in this combination, to the known extractive media for this process: 1, it does not form an azeotropic mixture with HFP and HFPO, 2. it is still in a liquid state at the boiling point of HFP and HFPO. 3. under the operating conditions, it does not undergo and kind of chemical reaction with HFP or HFPO, 4. under normal pressure, it has the low boiling point of 40° C., which also means a saving in energy. 5. it is cheap and readily obtainable, 6. it is not combustible, 7. under the operating conditions, it withstands even repeated exposure to heat, and 8. it is harmless from a toxicological point of view.

The process according to the invention is appropriately carried out by a continuous procedure, as follows: the gas mixture to be separated is fed to the lower section of an absorption column having 20 to 50 theoretical plates. Liquid methylene chloride flows downward in this absorptions column, which can, for example, be constructed as a packed column or as a bubble-cap plate column. The HFPO, which is less soluble in methylene chloride, is taken off in a fairly concentrated state at the head of the absorption column, whereas the HFP dissolves in the methylene chloride. On leaving the absorption column, the HFP-rich methylene chloride is conveyed to a column which has about 10 theoretical plates and which is equipped with heating in the sump. The methylene chloride is heated to the boil in this column. The dissolved HFP is thus evolved and is taken off at the head of this column. The degassed methylene chloride is then cooled again to the desired absorption temperature and is recycled to the head of the absorption column.

The absorption process is appropriately carried out within a temperature range from $-20°$ C. to $+30°$ C., preferably from $+15°$ C. to $+25°$ C. Absorption and desorption can be carried out under the same pressure. In order to adjust the pressure in both columns to the same value, the head of the desorption column can be connected to the lower section of the absorption column via a pressure equalization line.

The pressure applied is not in itself critical and can be within the range from 0.8 to 7 bar (absolute). The upper pressure limit for carrying out the process should be such that the liquefaction pressure of HFP and HFPO is not reached at the prevailing working temperature.

The quantity of methylene chloride to be circulated is essentially determined, at a given number of theoretical plates, by the absorption temperature and the desired degree of purity of the HFPO and HFP product streams.

Cooling water is appropriately employed as the most cost-effective cooling medium for cooling the recycled methylene chloride. An absorption temperature within the range from $15°$ to $25°$ C. is achieved if cooling water is used. Within this temperature range, 75 to 125 kg of methylene chloride per kg of HFPO/HFP mixture to be separated are required for the separation process.

It has been found that, under the operating conditions of the process according to the invention, methylene chloride is absolutely stable for long-term operation and can be employed for one year or longer without regeneration and without its separating action being impaired in any way. For long-term operation, methylene chloride is superior to the ethers described earlier in the text. These ethers are also less suitable as an extractive medium for the separation of HFPO/HFP mixtures because they undergo a slow chemical change under the operating conditions. The reaction products formed must, therefore, be discharged and replaced by fresh extractive medium from time to time.

The invention is illustrated in greater detail in the following examples:

EXAMPLE 1

7 kg/hour of a gas mixture composed of 89% by weight of HFP and 11% by weight of HFPO were fed to an absorption column having an internals diameter of 100 mm and a height of 7 m, packed with Raschig rings of diameter 10 mm. The feed point was 3 m above the bottom of the absorption column. 662 kg/hour of methylene chloride, which was cooled to $+22°$ C. with cooling water, were introduced at the head of the absorption column. The pressure in the absorption column was 1.7 bar (absolute). The HFPO product stream evolved at the head of the absorption column still contained methylene chloride which had been entrained in proportion to its partial pressure. This methylene chloride was removed in a small distillation column placed downstream, which was operated at a reflux ratio of 1:1. The methylene chloride-free HFPO product stream of 720 g/hour contained 98.6% by weight of HFPO and 1.4% by weight of HFP.

The hexafluoropropylene-rich methylene chloride leaving the bottom of the absorption column was introduced at the mid-point of a desorption column 3 m in length. The desorption column had the same diameter and the same packing as the absorption column. The head of the desorption column was connected to the lower section of the absorption column by means of a pressure equalization line. The desorption column was equipped with a forced-circulation reboiler in which the methylene chloride was heated to the boil. At the head of the desorption column there was a condenser through which cooling brine circulated, which re-condensed the methylene chloride evaporated in the forced-circulation reboiler and part of the HFPP. 6280 g/hour of a gaseous product containing 99% by weight of HFP and 1.0% by weight of HFPO were taken off above the condenser.

EXAMPLE 2

The procedure was exactly the same as in Example 1, with the difference that the HFPO/HFP mixture fed to the absorption column contained 62% by weight of HFPO and 38% by weight of HFP. The gaseous product taken off at the head of the absorption column at a rate of 4335 g/hour contained 99% by weight of HFPO and 1% by weight of HFP. 2665 g/hour of a gaseous product composed of 98.2% by weight of HFP and 1.8% by weight of HFPO were taken off above the head of the desorption column.

EXAMPLE 3

The procedure followed was analogous to that of Example 2, but the quantity of methylene chloride recycled was increased from 662 kg/hour to 875 kg/hour.

The product stream taken off, at a rate of 4338 g/hour, at the head of the absorption column contained 99.6% by weight of HFPO and 0.4% by weight of HFP. 2662 g/hour of a product composed of 99.3% by weight of HFP and 0.7% by weight of HFPO were taken off at the head of the desorption column.

I claim:

1. A process for the removal of hexafluoropropylene oxide from gas mixtures composed of hexafluoropropylene oxide and hexafluoropropylene by extractive distillation in the presence of an extractive medium, which comprises bringing the gas mixture into contact with methylene chloride as the extractive medium, whereupon hexafluoropropylene oxide is evolved in the form of gas and hexafluoropropylene is absorbed and is then liberated by heating the methylene chloride to its boiling point.

* * * * *